(12) United States Patent
Siedler et al.

(10) Patent No.: US 11,299,442 B2
(45) Date of Patent: Apr. 12, 2022

(54) PROCESS FOR PRODUCING ACETYLENE AND ETHYLENE

(71) Applicant: UOP LLC, Des Plaines, IL (US)

(72) Inventors: Nathan Siedler, Palatine, IL (US); Charles Luebke, Mount Prospect, IL (US); David Wegerer, Des Plaines, IL (US); Parag Jain, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/218,394

(22) Filed: Mar. 31, 2021

(65) Prior Publication Data

US 2021/0300840 A1 Sep. 30, 2021

Related U.S. Application Data

(60) Provisional application No. 63/002,955, filed on Mar. 31, 2020.

(51) Int. Cl.
| | | |
|---|---|---|
| *C07C 1/12* | (2006.01) | |
| *B01D 53/047* | (2006.01) | |
| *C07C 2/78* | (2006.01) | |
| *C07C 11/04* | (2006.01) | |
| *C07C 9/04* | (2006.01) | |
| *C07C 11/24* | (2006.01) | |

(52) U.S. Cl.
CPC ............. *C07C 1/12* (2013.01); *B01D 53/047* (2013.01); *C07C 9/04* (2013.01); *C07C 11/04* (2013.01); *C07C 11/24* (2013.01); *B01D 2257/108* (2013.01)

(58) Field of Classification Search
None
See application file for complete search history.

(56) References Cited

U.S. PATENT DOCUMENTS

| | | | | |
|---|---|---|---|---|
| 2005/0065392 | A1* | 3/2005 | Peterson | C07C 2/78 585/324 |
| 2014/0058149 | A1* | 2/2014 | Negiz | B01J 4/002 585/254 |
| 2014/0163287 | A1* | 6/2014 | Keusenkothen | C07C 4/04 585/501 |
| 2018/0111886 | A1* | 4/2018 | Gattupalli | B01J 8/0242 |

* cited by examiner

*Primary Examiner* — Philip Y Louie
(74) *Attorney, Agent, or Firm* — Paschall & Associates, LLC; Mark Goldberg

(57) ABSTRACT

A process for producing acetylene, ethylene, or both is disclosed. The process includes combusting a fuel stream to produce a combustion gas effluent stream and pyrolyzing a feed stream in a pyrolysis zone in the presence of the combustion gas effluent stream to produce a pyrolysis zone effluent stream which is further quenched and compressed. The compressed quenched stream is separated in a solvent separation column to produce a net gas stream comprising hydrogen, methane, and at least one carbon oxide and a product stream. A portion of the carbon oxide of the net gas stream is converted into methane in a methanation reactor and a reactor effluent stream is sent to an amine scrubber where carbon dioxide is removed and a methane containing stream is generated as an effluent. The methane containing stream is then recycled to the pyrolysis zone of the supersonic reactor.

13 Claims, 3 Drawing Sheets

PROCESS FOR PRODUCING ACETYLENE AND ETHYLENE

This application claims priority to provisional application 63/002,955, filed Mar. 31, 2020.

FIELD

System and process for converting a feed stream to acetylene or ethylene using a supersonic flow reactor including using a methanation reactor to generate and recycle methane.

BACKGROUND

Light olefin materials, including ethylene and propylene, represent a large portion of the worldwide demand in the petrochemical industry. Light olefins are used in the production of numerous chemical products via polymerization, oligomerization, alkylation and other well-known chemical reactions. These light olefins are essential building blocks for the modern petrochemical and chemical industries. Producing large quantities of light olefin material in an economical manner, therefore, is a focus in the petrochemical industry. The main source for these materials in present day refining is the steam cracking of petroleum feeds.

The cracking of hydrocarbons brought about by heating a feedstock material in a furnace has long been used to produce useful products, including for example, olefin products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50-55% for ethane compared to 25-30% for naphtha); however, the cost of the feedstock is more likely to determine which is used. Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production.

Recently, attempts have been made to use pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported. The liquids ultimately produced include naphtha, gasoline, or diesel. While this process may be effective for converting a portion of natural gas to acetylene or ethylene, it is estimated that this approach will provide only about a 40% yield of acetylene from a methane feed stream. While it has been identified that higher temperatures in conjunction with short residence times can increase the yield, technical limitations prevent further improvement to this process in this regard.

Compression cost is a major contributor towards the increase in methane conversion process economics. There is a need to optimize the compression profile of the conversion processes resulting in decreased utilities and overall improved economics. While the foregoing traditional combustion and pyrolysis systems provide solutions for converting ethane and propane into other useful hydrocarbon products, they have proven either ineffective or uneconomical for converting methane into these other products, such as, for example ethylene. The CO and CO2 were carried through the compressors, thereby increasing the overall unit compression costs and resulting in a large CO2 acid gas waste stream production.

Due to continued increases in the price of feeds for traditional processes, such as ethane and naphtha, and the abundant supply and corresponding low cost of natural gas and other methane sources available, for example the more recent accessibility of shale gas, it is desirable to provide commercially feasible and cost effective ways to use methane as a feed for producing ethylene and other useful hydrocarbons. Therefore, for a cost effective, efficient and economical conversion of methane into acetylene or ethylene, a methanation reactor can be used integrally with a supersonic reactor. There is a need for a unique conversion system including a methanation reactor, a combustion reactor, a pyrolysis reactor, a quench unit and a compression unit all integrated for increased methane conversion and acid gas removal thereby meeting the cost effectiveness of the conversion system. Other desirable features and characteristics of the present subject matter will become apparent from the subsequent detailed description of the subject matter and the claims, taken in conjunction with the accompanying drawing and this background of the subject matter.

SUMMARY

Various embodiments of an improved processes for converting feed stream into hydrocarbon compounds are provided. The process includes reacting a methane feed in a supersonic reactor to produce a reactor effluent that is solvent separated as well as hydrogenated to produce hydrogen and net gas. The net gas is processed in a methanation and amine scrubber installation where excess carbon oxide is converted into methane and the methane is then recycled to the supersonic reactor for further conversion.

In accordance with an exemplary embodiment, a process is provided for producing acetylene, ethylene, or both, the process comprising combusting a fuel stream in a combustion zone of a supersonic reactor to produce a combustion gas effluent stream. A feed stream is pyrolyzed in a pyrolysis zone of the supersonic reactor in the presence of the combustion gas effluent stream to produce a pyrolysis zone effluent stream. The pyrolysis zone effluent stream is then quenched in a quenching zone to produce a quenched stream. The quenched stream is further compressed in a compressor to form a compressed quenched stream. The compressed quenched stream is separated in a solvent separation column into a product stream and a net gas stream, the net gas stream comprising hydrogen, methane, and at least one carbon oxide. At least a portion of the carbon oxide of the net gas stream is converted in a methanation reactor into a methanation reactor effluent stream comprising primarily methane and carbon dioxide. The methanation reactor effluent stream is sent to an amine scrubber where carbon dioxide is removed and a methane containing stream is generated as an effluent. The methane containing stream is then recycled to the pyrolysis zone of the supersonic reactor.

In accordance with another exemplary embodiment, a process is provided for converting a carbon oxide into methane in an acetylene or ethylene production process, the process comprising separating a supersonic reactor effluent from a supersonic reactor in a solvent separation column to provide a product stream comprising acetylene, or ethylene, or both and a net gas stream comprising hydrogen, methane and at least one carbon oxide. Hydrogen is recovered from a first portion of the net gas stream from a pressure swing adsorption zone. At least one carbon oxide of a second portion of the net gas stream is converted into methane in a methanation reactor with a methanation reactor effluent produced and a carbon dioxide stream is removed from the methanation reactor effluent in an amine scrubber generating a methane containing stream. The methane containing stream is recycled to the supersonic reactor.

In accordance with yet another exemplary embodiment, is provided a system for the production of acetylene, ethylene, or both, the system comprising a supersonic reactor, a solvent separation column containing a solvent and in fluid communication with the supersonic reactor, a product stream conduit and a net gas stream conduit, a methanation reactor containing a methanation catalyst and in fluid communication with the net gas stream conduit and a methanation reactor effluent conduit, an amine scrubber in fluid communication with the methanation reactor effluent conduit and a carbon dioxide stream conduit and a methane containing stream conduit, wherein the methane containing stream conduit is in further fluid communication with the supersonic reactor.

These and other features, aspects, and advantages of the present disclosure are further explained by the following detailed description, drawing and appended claims.

BRIEF DESCRIPTION OF THE DRAWINGS

The various embodiments will hereinafter be described in conjunction with FIGS. 1-3, wherein like numerals denote like elements.

Figure 1:
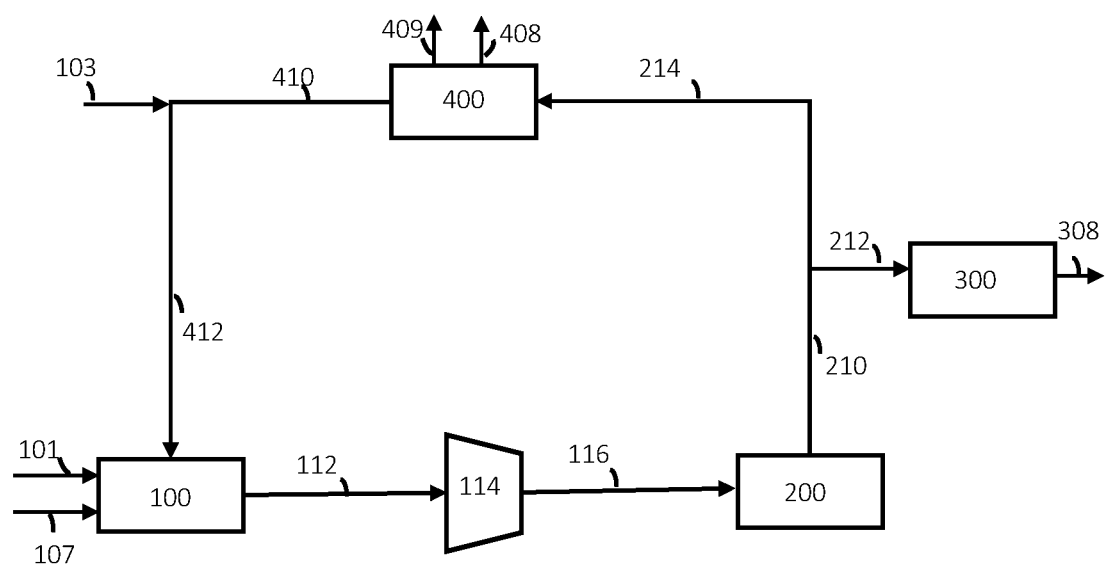
FIG. 1 is a schematic view of a system and process for converting feed and fuel into hydrocarbon products with a recycle treatment in accordance with various embodiments described herein.
Figure 2:
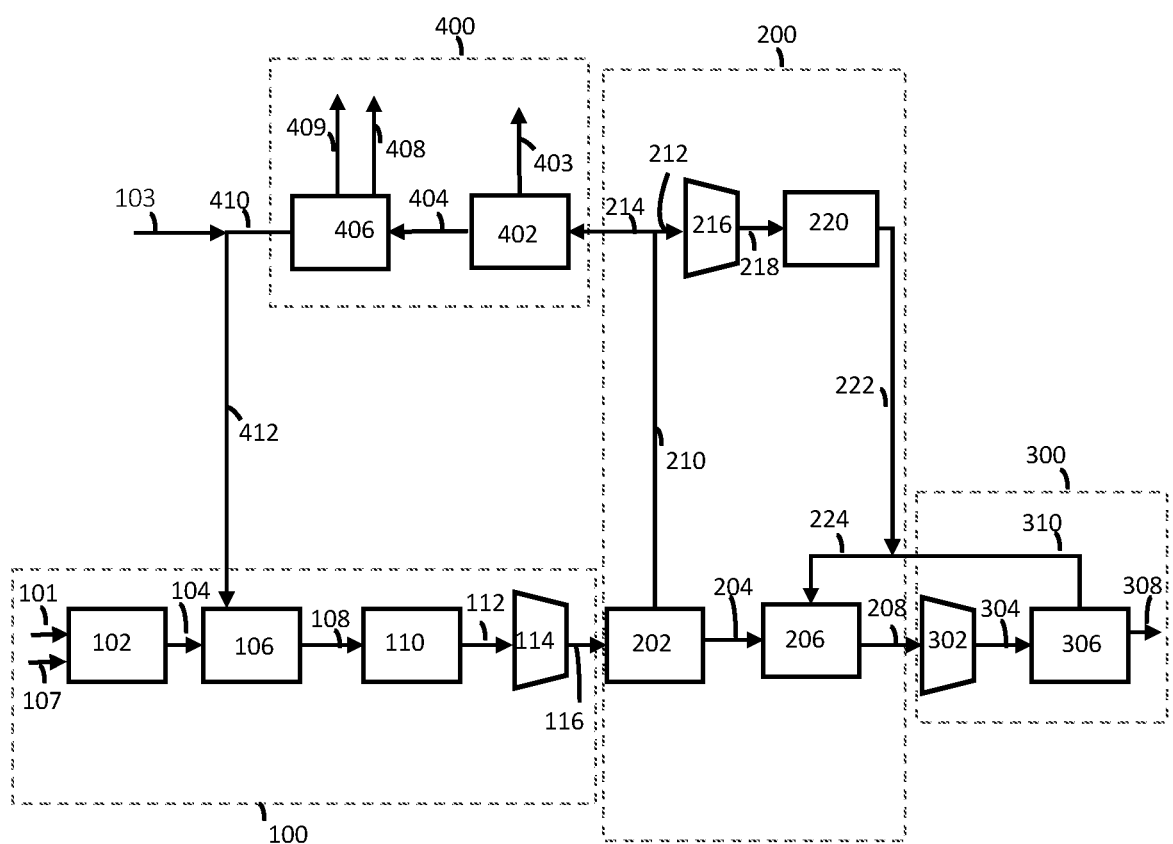
FIG. 2 is a schematic view of a system and process for converting methane into acetylene or ethylene and other hydrocarbon products in accordance with various embodiments described herein.
Figure 3:
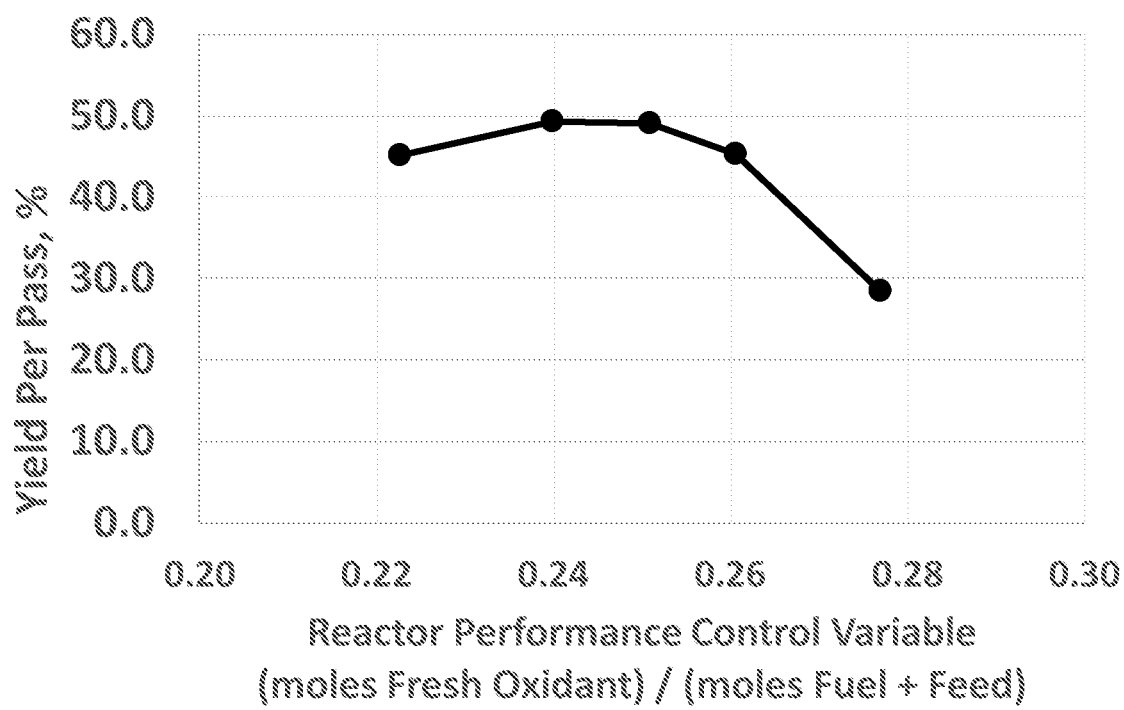
FIG. 3 is a depicts the performance and yield as achieved by the process for converting methane into acetylene and other hydrocarbon products in accordance with various embodiments described herein.

Skilled artisans will appreciate that elements in FIG. 1-3 are illustrated for simplicity and clarity and have not necessarily been drawn to scale. Also, common but well-understood elements that are useful or necessary in a commercially feasible embodiment may not be depicted in order to facilitate a less obstructed view of these various embodiments of the present disclosure.

DETAILED DESCRIPTION

Many variations of supersonic and shockwave reactors previously exist in the prior art. These processes include combusting a feedstock or carrier fluid in an oxygen-rich environment to increase the temperature of the feed and accelerate the feed to supersonic speeds. A shock wave is created within the reactor to initiate pyrolysis or cracking of the feed. However, one proposed alternative for the olefin production process may include using a methanation unit and a compression unit along with the supersonic reactor for methane conversion and acid gas removal from the methanation unit.

A system and process for converting hydrocarbon components in methane feed streams using a supersonic reactor is generally disclosed in previously cited references. As used herein, the term "methane feed stream" implies a feed stream comprising methane. The methane feed streams provided for processing in the supersonic reactor generally include methane and form at least a portion of a process stream. The system and process presented herein convert at least a portion of the methane to a desired product hydrocarbon compound to produce a product stream having a higher concentration of the product hydrocarbon compound relative to the feed stream.

The term "hydrocarbon stream" as used herein refers to one or more streams that provide at least a portion of the methane feed stream entering the supersonic reactor as described herein or are produced from the supersonic reactor from the methane feed stream, regardless of whether further treatment or processing is conducted on such a hydrocarbon stream. The "hydrocarbon stream" may include the methane feed stream, a supersonic reactor effluent stream, a desired product stream exiting a downstream hydrocarbon conversion process or any intermediate or by-product streams formed during the processes described herein. The hydrocarbon stream may be carried via a process stream which includes lines for carrying each of the portions of the process stream described herein. The term "process stream" as used herein includes the "hydrocarbon stream" as described above, as well as it may include a carrier fluid stream, a fuel stream, an oxygen source stream, or any streams used in the systems and the processes described herein.

Prior attempts to convert light paraffin or alkane feed streams, including ethane and propane feed streams, to other hydrocarbons using supersonic flow reactors have shown promise in providing higher yields of desired products from a particular feed stream than other more traditional pyrolysis systems. Specifically, the ability of these types of processes to provide very high reaction temperatures with very short associated residence times offer significant improvement over traditional pyrolysis processes. It has more recently been realized that these processes may also be able to convert methane to acetylene and other useful hydrocarbons, whereas more traditional pyrolysis processes were incapable or inefficient for such conversions.

Many flow schemes were discussed in the past where high volumes of carbon monoxide (CO) and carbon dioxide (CO2) gases were obtained from the pyrolysis zone of the shockwave reactor and the produced gases (CO & CO2) were required to be carried through the compressors thereby leading to increases in compression duty and cost. Applicants have now found an improved flow scheme where the amount of waste or acid gases produced is reduced. Previously, the entire net gas stream downstream of the acetylene absorber column was sent to a water gas shift reactor, and then to a pressure swing adsorption vessel to separate into hydrogen and a dirty recycle methane tail gas stream. Both the tail gas and the hydrogen combustor fuel needed to be compressed further to reach their destinations. With the improved process, herein, the net gas stream is only compressed enough to be recycled to the pyrolysis zone of the supersonic reactor.

When the supersonic reactor is used to make ethylene, the net gas stream sent to the pressure swing adsorption zone is what is needed for acetylene hydrogenation. At the same time if acetylene is the desired product, all pressure swing adsorption related equipment is then no longer required, saving. Thus, the syngas produced by the supersonic reactor is unsuitable for direct use in a methanol unit due to its high methane content. This methane either needs to be separated from the syngas mixture containing CO, CO2, and H2 or it needs to be converted further by using an auxiliary reformer unit. Both these options are energy intensive and are generally uneconomical when compared with just making syngas.

System and process for converting methane containing hydrocarbon streams to acetylene and other products are provided herein and have been identified to improve the overall process for the pyrolysis of light alkane feeds, including methane feeds, to acetylene and other useful products. The system and processes described herein also improves the ability of the system and associated components and equipment thereof to withstand degradation and possible failure due to extreme operating conditions within the reactor. The system and process described herein help achieve desired compression profiles of the supersonic and methane recycle system and process thereby resulting in decreased reliability on utilities and overall improvement in process economics.

In accordance with one approach, the system and process disclosed herein are used to treat a hydrocarbon process stream to convert at least a portion of methane in the hydrocarbon process stream to acetylene or ethylene or both as desired. While the hydrocarbon process stream must contain methane, it is envisioned the stream may also contain ethane and propane. In one approach, the hydrocarbon process stream is natural gas. The natural gas may be provided from a variety of sources including, but not limited to, gas fields, oil fields, coal fields, fracking of shale fields, biomass, and landfill gas. In another approach, the hydrocarbon process stream can include a stream from another portion of a refinery or processing plant. For example, light alkanes, including methane, are often separated during processing of crude oil into various products and a methane feed stream may be provided from one of these sources. These streams may be provided from the same refinery or different refinery or from a refinery off gas. The hydrocarbon process stream may include a stream from combinations of different sources as well.

A methane feed stream may be provided from a remote location or at the location or locations of the systems and process described herein. For example, while the methane feed stream source may be located at the same refinery or processing plant where the processes and systems are carried out, such as from production from another on-site hydrocarbon conversion process or a local natural gas field, the methane feed stream may be provided from a remote source via pipelines or other transportation process. For example, a feed stream may be provided from a remote hydrocarbon processing plant or refinery or a remote natural gas field, and provided as a feed to the systems and processes described herein. Initial processing of a methane stream may occur at the remote source to remove certain contaminants from the methane feed stream. Where such initial processing occurs, it may be considered part of the systems and processes described herein, or it may occur upstream of the systems and processes described herein. Thus, the methane feed stream provided for the systems and processes described herein may have varying levels of contaminants depending on whether initial processing occurs upstream thereof.

In one example, the methane feed stream has a methane content ranging from about 65 mol % to about 100 mol %. In another example, the concentration of methane in the hydrocarbon feed ranges from about 80 mol % to about 100 mol % of the hydrocarbon feed. In yet another example, the concentration of methane ranges from about 90 mol % to about 100 mol % of the hydrocarbon feed.

In one example, the concentration of ethane in the methane feed ranges from about 0 mol % to about 35 mol % and in another example from about 0 mol % to about 10 mol %. In one example, the concentration of propane in the methane feed ranges from about 0 mol % to about 5 mol % and in another example from about 0 mol % to about 1 mol %.

The methane feed stream may also include heavy hydrocarbons, such as aromatics, paraffinic, olefinic, and naphthenic hydrocarbons. These heavy hydrocarbons if present will likely be present at concentrations of between about 0 mol % and about 100 mol %. In another example, they may be present at concentrations of between about 0 mol % and 10 mol % and may be present at between about 0 mol % and 2 mol %.

System and process for methane conversion includes the addition of a methanation unit, whereby, the usage of natural gas combustor fuel is thus made economical. This reduces the overall amount of processing needed for the net gas, resulting in cost saving for the whole conversion process. There is also a reduction in the oxygen requirement and the net acid gas waste stream. The improved flow scheme for the overall methane conversion is thus compatible for both acetylene and ethylene production from methane or natural gas feeds. These processes can be used in all sort of techno-economical evaluations for the related technology. An example of the new flow scheme for methane conversion is shown in FIG. 1 which includes a supersonic reactor unit 100, a compressor unit 114, a solvent separation and selective hydrogenation unit 200, a product fraction unit 300 and a recycle treatment unit 400.

In accordance with an exemplary embodiment as shown in FIG. 1, a fuel stream comprising natural gas or methane is supplied in line 107 to a combustion zone of the supersonic reactor. A separate oxygen stream is also supplied in line 101 to the combustion zone of the supersonic reactor. The oxygen source can be from and an air separation unit (not shown here). The fuel stream in line 107 can optionally be pre-heated before passing it to the supersonic reactor 100. The fuel stream in line 107 is combusted in presence of oxygen in the combustion zone of the supersonic reactor to generate a combusted stream which is also called flue gas. This flue gas can provide energy for pyrolysis of the generated combusted stream in a pyrolysis zone of the supersonic reactor. The pyrolysis zone generates a process stream which is then quenched in a quench zone of the supersonic reactor 100. The supersonic reactor effluent in line 112 is passed to a compressor 114 to produce a compressed quenched stream in line 116. The reactor effluent stream in line 112 comprise a flue gas stream, a lighter hydrocarbon stream, a hydrogen stream, water, and a mixture thereof. The flue gas stream primarily comprises carbon oxide, carbon di-oxide and water in an amount of about 40 mole % to about 60 mole %. The lighter hydrocarbon stream constitutes acetylene and hydrogen in an amount of about 30 mole % to about 50 mole % collected as main products. In addition, the lighter hydrocarbon stream may also, optionally comprise at least 5 mole % of minor products such as ethylene, ethane, C3+ components, etc. and a remaining amount of unconverted methane. The reactor effluent stream in line 112 after passing through the combustion zone of the supersonic reactor 100 is passed to a compressor unit 114, located downstream of the supersonic reactor 100. The compressed quenched stream in line 116 is passed to the solvent separation and selective hydrogenation unit 200. The effluent from the solvent separation and selective hydrogenation unit 200, is obtained in line 210 which is split into a product stream in line 212 and a net gas stream in line 214. The product stream in line 212 is sent to the product fractionation unit 300 to generate a final product streams in line 308.

The net gas stream in line 214 is passed to the recycle treatment unit 400. In the recycle treatment unit 400, direct methanation of net gas stream 214 takes place without any need for further separation of hydrocarbon stream except the carbon oxides separation. The net gas stream in line 214 may comprise carbon oxides such as carbon monoxide, and/or carbon dioxide, hydrogen gas, methane and a mixture thereof. The methane content of the net gas stream 214 is substantially more than the amount of carbon oxides or hydrogen gas. The methane content can be in an amount of about 30 wt % to about 50 wt % of the total net gas stream recovered in line 214 obtained from the solvent separation and selective hydrogenation unit 200.

In accordance with an exemplary embodiment as shown in FIG. 1, carbon dioxide is desired to be separated out from the recycle treatment unit 400. The separated carbon dioxide stream is shown in line 408 in FIG. 1. Alongside, a separate high pressure steam stream can also be generated from the recycle treatment unit 400 (not shown here), which can be used to run the compression units of the overall system. A portion of the combusted fuel stream is also recovered separately in line 409 as an unreacted fuel stream, parallel to the carbon dioxide stream in line 408. The main purpose for the recycle treatment unit is to focus on more methane conversion and recycle along with the hydrogen recycle loop. The hydrogen stream generated in the net gas stream can be recycled to the solvent separation and selective hydrogenation unit 200 for any further separation. The effluent from the recycle treatment unit 400 majorly comprise methane gas recovered in line 410 which can be recycled to the pyrolysis zone of the supersonic reactor 100 as a recycled methane gas stream in line 410. The recycled methane gas stream in line 410 is combined with fresh methane gas stream supplied in line 103 to form a combined methane feed stream and supplied in line 412 to supersonic reactor for any further conversion into hydrocarbon products.

As illustrated in FIG. 1 the supersonic reactor is a single reactor including various components as described above. It should therefore be understood that the supersonic reactor may be formed modularly or as individual vessels. If formed modularly or as individual components, the modules or individual components of the supersonic reactor may be joined together permanently or temporarily, or may be separate from one another with fluids contained by other means, such as, for example, differential pressure adjustment between them. The separate or individual components of the supersonic reactor are further described herein and illustrated in FIG. 2.

In accordance with an exemplary embodiment as shown in FIG. 2, the supersonic reactor 100 includes a combustion zone 102, for combusting a fuel stream in line 107 to produce a carrier fluid along with a combustion zone effluent stream in line 104 at desired temperature and flowrate. The combustion zone may optionally include one or more fuel injectors (not shown) for injecting or supplying a fuel for combustion in line 107, comprising primarily of methane or natural gas. The same or other injectors may also be used for injecting or supplying an oxygen stream via line 101 to the combustion zone 102 for facilitating combustion reaction. It is noted that the injection of fuel stream in line 107 and separate oxygen stream in line 101, can be done in an axial direction, tangential direction, radial direction, or other direction, including a combination of directions. The fuel and oxygen streams are combusted to produce an effluent stream comprising a hot carrier fluid stream along with the combustion zone effluent stream in line 104, typically having a temperature of from about 1200° C. to about 3500° C. in one example, between about 2000° C. and about 3500° C. in another example, and between about 2500° C. and about 3200° C. in yet another example. It is also contemplated herein to produce the hot carrier fluid stream by other known processes, from the combustion zone 102 including non-combustion processes. Per one example the carrier fluid stream has a pressure of about 1 atm or higher, greater than about 2 atm in another example, and greater than about 4 atm in another example.

The hot carrier fluid stream along with the combustion zone effluent stream in line 104 as produced from the combustion zone 102 of the supersonic reactor 100 is then passed to a pyrolysis zone 106 of the supersonic reactor 100. In the pyrolysis zone 106 further conversion and pyrolysis of a feed stream takes place in the presence of the carrier fluid and the combustion gas effluent stream in line 104 to produce a pyrolysis zone effluent stream in line 108. The velocity of the hot carrier fluid stream is accelerated to above about Mach 1.0 in one example, between about Mach 1.0 and Mach 4.0 in another example, and between about Mach 1.5 and 3.5 in another example, in the pyrolysis zone. In this regard, the residence time of the carrier fluid stream in line 104 within the pyrolysis zone 106 is between about 0.5 and 100 ms in one example, about 1.0 and 50 ms in another example, and about 1.5 and 20 ms in another example. The temperature of the carrier fluid stream in line 104 is between about 1000° C. and about 3500° C., between about 1200° C. and about 2500° C. in another example, and between about 1200° C. and about 2000° C. in another example.

In another exemplary embodiment, in the pyrolysis zone 106 a recycled combined methane feed stream is provided in line 103 to be mixed with the hot carrier fluid stream and the combustion zone effluent stream in line 104 and react within the pyrolysis zone 106. The methane feed stream may be injected via one or more feed injectors into the reaction chamber of the pyrolysis zone 106. In the pyrolysis zone 106 there is a rapid reduction in the velocity of the gases flowing therethrough to convert the kinetic energy of the flowing fluid to thermal energy to further heat the feed stream to cause rapid pyrolysis of the methane containing feed stream.

The hot fluid produced from the pyrolysis zone is known as pyrolysis zone effluent stream in line 108 is passed to a quenching zone 110 of the supersonic reactor 100 where the pyrolysis zone effluent stream is quenched to generate a quenched stream in line 112. Another reason to quickly quench pyrolysis zone effluent stream in the quenching zone 110 is to stop the pyrolysis reaction from further conversion of the desired acetylene or ethylene product streams to other compounds. In the quenching zone 110, spray bars may be used to introduce quenching liquid, such as water or steam.

The supersonic reactor effluent stream or the quenched stream exits in line 112 and forms a portion of the hydrocarbon stream. The quenched stream in line 112 may include a larger concentration of acetylene or ethylene as compared to feed stream concentration and a reduced concentration of methane relative to the feed stream. The quenched stream in line 112 may also be referred to herein as an acetylene containing stream or an ethylene containing stream as it includes an increased concentration of acetylene or ethylene or a mixture thereof. The quenched stream in line 112 may also be considered as an intermediate stream produced in a process to form another hydrocarbon product or it may be further processed and captured as product stream.

The quenched stream in line 112 is passed to a compressor unit 114 where the stream is compressed at a moderate pressure condition to generate a compressed quenched stream in line 116. The compression of the quenched stream occurs typically at a pressure of from about 0 psig to 220 psig in one example, between about 20 psig to about 200 psig in another example, and between about 30 psig to about 185 psig in yet another example. The compressed quenched stream in line 116 is passed to a solvent separation column 202 where the compressed quenched stream is separated into a net gas stream and a product stream. The net gas stream is generated in line 210 and the product stream is generated in line 204. The net gas stream in line 210 comprises a carbon oxide, hydrogen and a methane stream, wherein the carbon oxide may include at least one of carbon dioxide or carbon monoxide or a combination thereof. In a further exemplified embodiment, the product stream in line 204 may include at least one of acetylene or ethylene or a mixture of acetylene or ethylene thereof.

The net gas stream in line 210 is split into two portions including a first portion in line 212 passed to a compressor 216 and a second portion in line 214 which is passed to a methanation reactor 402. In an embodiment, the first portion of the net gas stream in line 212 is passed to a compressor 216 to generate a compressed stream in line 218. The compressed stream in line 218 is then passed to a pressure swing adsorption zone 220 to generate a recycle hydrogen stream in line 222. It is found by the applicant, that the net gas is only compressed enough to be recycled to the pyrolysis zone of the supersonic reactor without hampering the compression duty.

In an example, at least a portion of hydrogen from the recycle hydrogen stream 222 is recovered to be used in the supersonic reactor. In another example, a portion of the hydrogen containing stream 224 recovered from the recycle hydrogen stream can also be passed to a selective hydrogenation reactor 206 via line 224 for use in product recovery unit. The product stream in line 204 and the hydrogen containing stream in line 224 are combined in the selective hydrogenation reactor 206 and selectively hydrogenated in the presence of a solvent stream to generate a product stream in line 208 comprising primarily hydrogen, methane, acetylene, ethylene, small quantities of carbon dioxide, or other hydrocarbons like C3 or C4 hydrocarbons or a mixture thereof in any proportion. An external stream of solvent can optionally be passed to the selective hydrogenation reactor 206 to selectively absorb the desired product such as acetylene or ethylene from the combined stream and pass on to for recovery. The used solvent can be recovered separately from the hydrogenation reactor for any further use.

In another embodiment, the product stream recovered in line 208 from the selective hydrogenation reactor 206 is passed to a compressor 302 of the product fractionation unit 300 to raise the pressure of the product stream from about 0 psig to about 700 psig in one example, from about 100 psig to about 700 psig in another example, and from about 300 psig to about 600 psig in a yet another example, to generate a compressed product stream in line 304. It is often contemplated that the compression costs are a major contributor to the reaction economics. In accordance with an exemplary embodiment, the compression profiles for the overall supersonic reaction is optimized resulting in overall decrease in utility requirements and overall improvements in economics.

The compressed product stream in line 304 is sent for final product separation and recovery in a product fractionation column 306 from where a final product stream in line 308 containing at least one of C2 or C3 or a mixture of C2 and C3 hydrocarbons are recovered along with a hydrogen product stream. As an example, the C2 hydrocarbon stream may further comprise acetylene or ethylene or a mixture thereof. The hydrogen product stream in line 310 can also be recycled for any further use to the selective hydrogenation reactor in line 310 along with the hydrogen containing stream 224 as shown in FIG. 2. The final product stream may optionally be passed to a dryer for removing any extra fluid such as water, steam, etc., from the product stream prior to sending the final product stream to the product fractionation column 306 in line 304.

In accordance with the exemplary embodiment as shown in FIG. 2, the second portion of the net gas stream sent in line 214 as recovered from the solvent separation column 202 is passed to a methanation reactor 402, where the carbon oxides and hydrogen contained in the net gas stream are converted to methane. Methanation of the net gas stream is done to purify the net gas stream and to recover more methane from the net gas stream to be used as a recycle pyrolysis feed stream. Along with methane, water or steam is also generated from the methanation reactor which can be taken out separately. The primary purpose of integrating the methanation reactor with the supersonic reactor is to utilize the excess amount of carbon oxides produced in the net gas stream and convert them into more methane. It was surprisingly found that integration of methanation and supersonic reactor resulted in improved carbon efficiency of the overall process from an estimated efficiency improvement of about 58% to nearly about 65% while improving operational flexibility.

Exemplary methanation conditions includes a temperature from 200° C. to 300° C., a pressure of 10 bar to 20 bar and utilizes any of the Nickel containing catalysts which are available for the reaction in methanation reactor 402. The methanation reactor effluent stream in line 404 is passed to an amine scrubber 406 where the excess carbon dioxide is discarded as a separate stream or a flue gas stream in line 408. Applicants have found that by using an amine scrubber and the methanation reactor directly on the net gas recycle loop, any further separation of net gas components is suppressed except for the removal of residual carbon dioxide stream recovered and separated in line 408. The methanation reactor effluent stream in line 404 can also be used as a recycle feed to the pyrolysis zone. The methanation reactor effluent stream in line 404 consists mainly of a methane containing stream which is still required to be further purified as trace amounts of carbon dioxide or carbon monoxide or other acid gases may still be present. To remove the carbon oxides or acid gases from the methane containing stream in line 404 an amine gas is used within the amine scrubber 406 which selectively promotes the removal of acid gases or carbon oxides from methane. A separate stream of high pressure steam is also generated in line 409 coming out of the methanation reactor, which can be used to run any of the compressors in the system. The amine scrubber 406 generates an effluent stream comprising methane gas stream recovered in line 410 which can be recycled to the pyrolysis zone 106 of the supersonic reactor 100. The recycled methane gas stream can be supplied as recycled methane feed stream in line 410. A fresh methane feed stream in line 103 is also supplied to the pyrolysis reactor to increase the methane content of the feed stream for better conversion. The fresh methane feed stream in line 103 can be combined with the recycled methane feed stream in line 410 to form a combined methane feed stream in line 412 supplied to the pyrolysis reactor 106 for improved conversion of methane into hydrocarbon products.

It was found that around 60% by weight of the combined pyrolysis feed in line 412 supplied to the pyrolysis zone 106 was recovered from the amine scrubber and methanation reactor. The methane purity of 99.5% is achieved by applicants' invention, which enables purification of dirtier natural gas feeds to the pyrolysis reactor.

In one example, the pyrolysis effluent stream from the supersonic reactor 100 has a reduced methane content relative to the methane feed stream in line 107 ranging from about 15 mol % to about 95 mol %. In another example, the concentration of methane ranges from about 40 mol % to about 90 mol % and from about 45 mol % to about 85 mol % in another example.

In one example the yield of acetylene produced from methane in the feed in the supersonic reactor is between about 40% and about 95%. In another example, the yield of acetylene produced from methane in the feed stream is between about 50% and about 90%. Advantageously, this provides a better yield than the estimated 40% yield achieved from previous, more traditional, pyrolysis approaches.

By one approach, the supersonic reactor effluent stream flowing in line 112 is reacted to form product hydrocarbons. In this regard, the reactor effluent portion of the product hydrocarbons can be sent to a hydrocarbon conversion process for any further processing. While the reactor effluent stream may also undergo several intermediate process steps, such as, for example, water removal, adsorption, and/or absorption to provide a concentrated acetylene stream, these intermediate steps will not be described in detail herein.

In accordance with another exemplary embodiment, it is found that the methane conversion system as illustrated in FIG. 2 and described herein is a unique arrangement which allows the integrated supersonic and methanation reactor to run at a lower conversion rates while still maintaining the same operational costs of the system. as illustrated in FIG. 3, the conversion is determined as percentage (%) increase in yield per pass with respect to the increase in reactor performance controlled variable. In a preferred embodiment, schematic shown as FIG. 3 depicts the reactor performance control variable and yield of methane per pass. The yield per pass is defined as the conversion of feed times of the selectivity of the derived products.

Applicants have found that in a typical reactor-separator system heat is provided indirectly for the endothermic reactions, as heat input is lowered, conversion per pass is lowered causing higher recycle and therefore resulting higher utilities in downstream compression. However, as heat input is increased, conversion increases (usually at the cost of selectivity decreases), and downstream compression cost decreases. Typically, it is believed that the optimum for the overall process is generally the optimum based on yield per pass of the reactor section alone.

However, in the claimed invention, the reaction system, includes the heat carrier flue gases which are intermediately mixed with reactor products, therefore they cannot be independently optimized. For example, increase in the heat input improves the reactor conversion, but it may result in increased downstream gas processing due to increase in flow of heat carrying flue gases. Thus, the optimum yield of the reaction system alone is not the yield for the overall process, and is in fact a lower value.

Applicants have further found the higher yield per pass, more is the thermal energy used in the pyrolysis zone. Surprisingly, although higher yield points are undesirable because of the generation of a large amount of carbon dioxide and use of a large amount of pure oxygen. Reduction in yield means decreased carbon dioxide production with an increase in the recycle pyrolysis feed. With the net gas recycle to the methanation reactor as shown in FIG. 2, the compression costs across the compressor installed downstream of the supersonic reactor is essentially unaffected. This is because the volumetric flow at operating conditions at the suction of the compressor stays constant.

While there have been illustrated, and described in embodiments and aspects, it will be appreciated that numerous changes and modifications will occur to those skilled in the art, and it is intended in the appended claims to cover all those changes and modifications which fall within the true spirit and scope of the present disclosure and appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing acetylene, ethylene, or both, the process comprising combusting a fuel stream in a combustion zone of a supersonic reactor to produce a combustion gas effluent stream; pyrolyzing a feed stream in a pyrolysis zone of the supersonic reactor in the presence of the combustion gas effluent stream to produce a pyrolysis zone effluent stream; quenching the pyrolysis zone effluent stream to produce a quenched stream; compressing the quenched stream to form a compressed quenched stream; separating the compressed quenched stream in a solvent separation column into a product stream and a net gas stream, the net gas stream comprising hydrogen, methane, and at least one carbon oxide; converting a portion of the carbon oxide of the net gas stream in a methanation reactor, into methane and producing a methanation reactor effluent; removing a carbon dioxide stream from the methanation reactor effluent in an amine scrubber and generating a methane containing stream; and recycling the methane containing stream to the supersonic reactor. An embodiment of the invention is one, any or all prior embodiments in this paragraph up through the first embodiment in this paragraph, further comprising introducing a separate oxygen containing stream to the combustion zone. An embodiment of the invention is one, any or all of prior embodiments in this paragraph up through the first embodiment in this paragraph, wherein the fuel stream supplied to the combustion zone comprises methane or pipeline natural gas. An embodiment of the invention is one, any or all of prior embodiments in this paragraph up through the first embodiment in this paragraph, wherein the feed stream to the pyrolysis zone of the supersonic reactor comprises a combined methane feed stream. An embodiment of the invention is one, any or all of prior embodiments in this paragraph up through the first embodiment in this paragraph, further comprising passing a fresh methane containing feed stream to the effluent line of an amine scrubber. An embodiment of the invention is one, any or all of prior embodiments in this paragraph up through the first embodiment in this paragraph, further comprising hydrogenating the product stream from the solvent separation column in a hydrogenation reactor to generate a hydrogenated product stream; compressing the hydrogenated product stream in a compressor to form a compressed hydrogenated product stream; separating the compressed hydrogenated product stream in a product fractionation column to provide a C2 and/or C3+ hydrocarbon stream and a hydrogen stream; and recycling the hydrogen stream from the product fractionation column to the hydrogenation reactor. An embodiment of the invention is one, any or all prior embodiments in this paragraph up through the first embodiment in this paragraph, further comprising drying the compressed product stream in a dryer prior to separating the compressed hydrogenated product stream to the product fractionation column. An embodiment of the invention is one, any or all of prior embodiments in this paragraph up through the first embodiment in this paragraph, further comprising compressing a portion of the net gas stream from the solvent separation column to form a compressed net gas stream; adsorbing the compressed net gas stream in a pressure swing adsorption zone to recover an adsorbed hydrogen stream; and recycling the adsorbed hydrogen stream to the hydrogenation reactor.

A second embodiment of the invention is a process for converting a carbon oxide into methane in an acetylene or ethylene production process, the process comprising separating a supersonic reactor effluent from a supersonic reactor in a solvent separation column to provide a product stream comprising acetylene, or ethylene, or both and a net gas stream comprising hydrogen, methane and at least one carbon oxide; sending a first portion of the net gas stream to a pressure swing adsorption zone to recover hydrogen to produce a hydrogen stream; sending a second portion of the net gas stream to a methanation reactor to convert at least one carbon oxide of the second portion of the net gas stream into methane and producing a methanation reactor effluent; removing a carbon dioxide stream from the methanation reactor effluent in an amine scrubber generating a methane containing stream; and recycling the methane containing stream to the supersonic reactor. An embodiment of the invention is one, any or all of prior embodiments in this paragraph up through the second embodiment in this paragraph, further comprising combusting a fuel stream in a combustion zone of the supersonic reactor to produce a combustion gas effluent stream; pyrolyzing a feed stream in a pyrolysis zone of the supersonic reactor in the presence of the combustion gas effluent stream to produce a pyrolysis zone effluent stream; and quenching the pyrolysis zone effluent stream to produce the supersonic reactor effluent. An embodiment of the invention is one, any or all of prior embodiments in this paragraph up through the second embodiment in this paragraph, further comprising hydrogenating the product stream in a hydrogenation reactor to generate a hydrogenated product stream; compressing the hydrogenated product stream in a compressor to form a compressed hydrogenated product stream; separating the compressed hydrogenated product stream in a product fractionation column to provide a C2 and/or C3+ hydrocarbon stream and a hydrogen stream; and recycling the hydrogen stream from the product fractionation column to the hydrogenation reactor. An embodiment of the invention is one, any or all of prior embodiments in this paragraph up through the second embodiment in this paragraph, further comprising compressing the first portion of the net gas stream in a compressor prior to sending the net gas stream to the pressure swing adsorption zone; and recycling the hydrogen in the hydrogen stream to the hydrogenation reactor. An embodiment of the invention is one, any or all of prior embodiments in this paragraph up through the second embodiment in this paragraph, further comprising compressing the supersonic reactor effluent in a compressor located upstream of the solvent separation column. An embodiment of the invention is one, any or all of prior embodiments in this paragraph up through the second embodiment in this paragraph, further comprising recycling the methane containing stream from the amine scrubber to the supersonic reactor. An embodiment of the invention is one, any or all of prior embodiments in this paragraph up through the second embodiment in this paragraph, further comprising introducing a methane containing stream to the amine scrubber effluent line.

A third embodiment of the invention is a system for producing acetylene, ethylene, or both, the system comprising a supersonic reactor; a solvent separation column containing a solvent and in fluid communication with the supersonic reactor, a product stream conduit and a net gas stream conduit; a methanation reactor containing a methanation catalyst and in fluid communication with the net gas stream conduit and a methanation reactor effluent conduit; an amine scrubber in fluid communication with the methanation reactor effluent conduit and a carbon dioxide stream conduit and a methane containing stream conduit; and the methane containing stream conduit in further fluid communication with the supersonic reactor. An embodiment of the invention is one, any or all of prior embodiments in this paragraph up through the third embodiment in this paragraph, further comprising a hydrogenation reactor in fluid communication with the solvent separation column and the product stream conduit; a compressor in downstream fluid communication with the hydrogenation reactor; a product fractionation column in downstream fluid communication with the compressor and in fluid communication with a C2 and/or C3+ hydrocarbon stream conduit and a hydrogen stream conduit; and the hydrogen stream conduit further in fluid communication with the hydrogenation reactor. An embodiment of the invention is one, any or all of prior embodiments in this paragraph up through the third embodiment in this paragraph, further comprising another compressor in fluid communication with the net gas stream conduit. An embodiment of the invention is one, any or all of prior embodiments in this paragraph up through the third embodiment in this paragraph, further comprising a pressure swing adsorption zone in fluid communication with another compressor and in fluid communication with the hydrogen stream conduit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise.

The invention claimed is:
1. A process for producing acetylene, ethylene, or both, the process comprising:

combusting a fuel stream in presence of oxygen in a combustion zone of a supersonic reactor to produce a combustion gas effluent stream;
pyrolyzing a feed stream in a pyrolysis zone of the supersonic reactor in the presence of the combustion gas effluent stream to produce a pyrolysis zone effluent stream;
quenching the pyrolysis zone effluent stream to produce a quenched stream;
compressing the quenched stream to form a compressed quenched stream;
separating the compressed quenched stream in a solvent separation column into a product stream and a net gas stream, the net gas stream comprising hydrogen, methane, and at least one carbon oxide;
converting a portion of the carbon oxide of the net gas stream in a methanation reactor, into methane and producing a methanation reactor effluent;
removing a carbon dioxide stream from the methanation reactor effluent in an amine scrubber and generating a methane containing stream; and
recycling the methane containing stream to the supersonic reactor,
wherein a mole ratio of oxygen to fuel and feed in the supersonic reactor varies between 0.223-0.26.

2. The process of claim 1, wherein the fuel stream supplied to the combustion zone comprises methane or pipeline natural gas.

3. The process of claim 1, wherein the feed stream to the pyrolysis zone of the supersonic reactor comprises a combined methane feed stream.

4. The process of claim 1, further comprising passing a fresh methane containing feed stream to the methane containing stream of the amine scrubber.

5. The process of claim 1, further comprising:
hydrogenating the product stream from the solvent separation column in a hydrogenation reactor to generate a hydrogenated product stream;
compressing the hydrogenated product stream in a compressor to form a compressed hydrogenated product stream;
separating the compressed hydrogenated product stream in a product fractionation column to provide a C2 and/or C3+ hydrocarbon stream and a hydrogen stream; and
recycling the hydrogen stream from the product fractionation column to the hydrogenation reactor.

6. The process of claim 5, further comprising drying the compressed product stream in a dryer prior to separating the compressed hydrogenated product stream to the product fractionation column.

7. The process of claim 5, further comprising:
compressing a portion of the net gas stream from the solvent separation column to form a compressed net gas stream;
adsorbing the compressed net gas stream in a pressure swing adsorption zone to recover an adsorbed hydrogen stream; and
recycling the adsorbed hydrogen stream to the hydrogenation reactor.

8. A process for converting a carbon oxide into methane in an acetylene or ethylene production process, the process comprising:
combusting a fuel stream in a combustion zone of a supersonic reactor to produce a combustion gas effluent stream;
pyrolyzing a feed stream in a pyrolysis zone of the supersonic reactor in the presence of the combustion gas effluent stream to produce a pyrolysis zone effluent stream;
quenching the pyrolysis zone effluent stream to produce a supersonic reactor effluent;
separating the supersonic reactor effluent from the supersonic reactor in a solvent separation column to provide a product stream comprising acetylene, or ethylene, or both and a net gas stream comprising hydrogen, methane and at least one carbon oxide;
sending a first portion of the net gas stream to a pressure swing adsorption zone to recover hydrogen to produce a hydrogen stream;
sending a second portion of the net gas stream to a methanation reactor to convert at least one carbon oxide of the second portion of the net gas stream into methane and producing a methanation reactor effluent;
removing a carbon dioxide stream from the methanation reactor effluent in an amine scrubber generating a methane containing stream; and
recycling the methane containing stream to the supersonic reactor,
wherein a mole ratio of oxygen to fuel and feed in the supersonic reactor varies between 0.223-0.26.

9. The process of claim 8, further comprising:
hydrogenating the product stream in a hydrogenation reactor to generate a hydrogenated product stream;
compressing the hydrogenated product stream in a compressor to form a compressed hydrogenated product stream;
separating the compressed hydrogenated product stream in a product fractionation column to provide a C2 and/or C3+ hydrocarbon stream and a hydrogen stream; and
recycling the hydrogen stream from the product fractionation column to the hydrogenation reactor.

10. The process of claim 9, further comprising:
compressing the first portion of the net gas stream in a compressor prior to sending the net gas stream to the pressure swing adsorption zone; and
recycling the hydrogen in the hydrogen stream to the hydrogenation reactor.

11. The process of claim 8, further comprising compressing the supersonic reactor effluent in a compressor located upstream of the solvent separation column.

12. The process of claim 8, further comprising recycling the methane containing stream from the amine scrubber to the supersonic reactor.

13. The process of claim 8, further comprising introducing a fresh methane containing stream to the methane containing stream of the amine scrubber.

* * * * *